US009931630B2

(12) United States Patent
Chu et al.

(10) Patent No.: US 9,931,630 B2
(45) Date of Patent: Apr. 3, 2018

(54) AUTONOMOUS AND PROGRAMMABLE SEQUENTIAL FLOW OF SOLUTIONS IN CAPILLARY MICROFLUIDICS

(71) Applicants: Virginia Chu, Lisbon (PT); Pedro José De Oliva Novo, Romãs (PT); João Pedro Estrela Rodrigues Conde, Lisbon (PT); Francesca Volpetti, Rome (IT)

(72) Inventors: Virginia Chu, Lisbon (PT); Pedro José De Oliva Novo, Romãs (PT); João Pedro Estrela Rodrigues Conde, Lisbon (PT); Francesca Volpetti, Rome (IT)

(73) Assignee: INSTITUTO DE ENGENHARIA DE SISTEMAS E COMPUTADORES PARA OS MICROSISTEMAS E AS NANOTECNOLOGIAS (INESC-MN), Lisboa (PT)

( * ) Notice: Subject to any disclaimer, the term of this patent is extended or adjusted under 35 U.S.C. 154(b) by 0 days.

(21) Appl. No.: 14/405,659

(22) PCT Filed: Jun. 5, 2013

(86) PCT No.: PCT/IB2013/054630
§ 371 (c)(1),
(2) Date: Dec. 4, 2014

(87) PCT Pub. No.: WO2013/183013
PCT Pub. Date: Dec. 12, 2013

(65) Prior Publication Data
US 2015/0165435 A1    Jun. 18, 2015

(30) Foreign Application Priority Data

Jun. 6, 2012 (PT) .................................... 106365

(51) Int. Cl.
*B01L 3/00* (2006.01)
*G01N 21/25* (2006.01)
(Continued)

(52) U.S. Cl.
CPC ....... *B01L 3/5027* (2013.01); *B01L 3/502715* (2013.01); *B01L 3/502784* (2013.01);
(Continued)

(58) Field of Classification Search
CPC ............ B01L 3/5027; B01L 3/502715; B01L 3/502784; G01N 21/76; G01N 21/6486; G01N 21/251
See application file for complete search history.

(56) References Cited

U.S. PATENT DOCUMENTS 7,491,272 B2    2/2009 Delamarche et al.
2002/0058273 A1*    5/2002 Shipwash ............. B01L 3/5027
435/6.12
(Continued)

FOREIGN PATENT DOCUMENTS

WO    2012054794 A1    4/2012

OTHER PUBLICATIONS

International Search Report for PCT Application No. PCT/IB2013/054630, dated Sep. 26, 2013; European Patent Office, Rijswijk, Netherlands.
(Continued)

*Primary Examiner* — Melanie Yu Brown
(74) *Attorney, Agent, or Firm* — Thomas E. Lees, LLC (57) ABSTRACT

Aspects of the present disclosure relate to a capillary fluidic device comprising at least two inlets, a microfluidic channel and an outlet. The device allows for the autonomous and programmable sequential flow of the same or different fluids using capillary fluidics for autonomous pumping of liquids to other downstream fluidic structures. External pumping
(Continued)

and valving systems are not required, thus reducing complexity and increasing portability of stand-alone microfluidic systems. Aspects of the present disclosure can be applied to other fluidic structures for performing analytical biological assays. The integration has at least one reaction chamber and at least one capillary pump. The device is integrated with at least one sensor for detection and quantification of the biological assay signals.

19 Claims, 7 Drawing Sheets (51) Int. Cl.
*G01N 21/64* (2006.01)
*G01N 21/76* (2006.01)

(52) U.S. Cl.
CPC ....... *G01N 21/251* (2013.01); *G01N 21/6486* (2013.01); *G01N 21/76* (2013.01); *B01L 2200/0621* (2013.01); *B01L 2200/0642* (2013.01); *B01L 2200/0673* (2013.01); *B01L 2400/0406* (2013.01); *G01N 2201/02* (2013.01); *G01N 2201/061* (2013.01); *Y10T 436/2575* (2015.01)

(56) References Cited

U.S. PATENT DOCUMENTS

| | | | |
|---|---|---|---|
| 2004/0189311 A1* | 9/2004 | Glezer | B01L 3/5027 324/444 |
| 2005/0249641 A1 | 11/2005 | Blankenstein et al. | |
| 2006/0093697 A1 | 5/2006 | Delamarche et al. | |
| 2006/0094119 A1 | 5/2006 | Ismagilov et al. | |
| 2008/0003572 A1 | 1/2008 | Delamarche et al. | |
| 2008/0145835 A1 | 6/2008 | Alajem et al. | |
| 2008/0273918 A1 | 11/2008 | Linder et al. | |
| 2008/0295909 A1 | 12/2008 | Locascio et al. | |
| 2009/0053106 A1 | 2/2009 | Wu et al. | |
| 2009/0130746 A1* | 5/2009 | Cao | B01L 3/502707 435/287.2 |
| 2009/0227007 A1* | 9/2009 | Takahashi | B01L 3/502715 435/287.2 |
| 2010/0196205 A1* | 8/2010 | Quinn | G01N 35/1095 422/82 |
| 2010/0239459 A1 | 9/2010 | Alajem et al. | |
| 2011/0120562 A1* | 5/2011 | Tan | B01L 3/50273 137/1 |
| 2012/0103427 A1 | 5/2012 | Park et al. | |
| 2012/0107805 A1 | 5/2012 | Neas et al. | |
| 2012/0136492 A1* | 5/2012 | Amin | B01F 5/102 700/285 |
| 2012/0196280 A1* | 8/2012 | Karlsen | B01L 3/5027 435/6.1 |

OTHER PUBLICATIONS

Written Opinion of the International Searching Authority for PCT Application No. PCT/IB2013/054630, dated Sep. 26, 2013; European Patent Office, Munich, Germany.

L. Gervais, N. de Rooij, E. Delamarche, "Microfluidic Chips for Point-of-Care Immunodiagnostics", Advanced Materials, 23 (2011), H151-H176.

L. Gervais, E. Delamarche, "Toward One-Step Point-of-Care Immunodiagnostics Using Capillary Driven Microfluidics and PDMS Substrates", Lab Chip, 9 (2009), 3330-3337.

P. B. Lillehoj, F. Wei, C-M. Ho, "A Self-Pumping Lab-on-a-Chip for Rapid Detection of Botulinum Toxin", Lab Chip, 10 (2010), 2265-2270.

C. D. Curtis, V. Linder, S. K. Sia, "Commercialization of Microfluidic Point-of-Care Diagnostic Devices", Lab Chip, 12 (2012), 2118-2134.

Detekt Biomedical L.L.C., "Lateral Flow Readers for Rapid Test Strip Detection and Immunoassays", http://www.idetekt.com/, (online) retrieved from https://web.archive.org/web/20120530005644/http://www.idetekt.com/, archive date of May 2012.

P. Novo, D.M.F. Prazeres, V. Chu, J. P. Conde, "Microspot-Based ELISA in Microfluidics: Chemiluminescence and Colorimetry Detection Using Thin-Film Hydrogenated Amorphous Silicon Photodiodes", Lab Chip, 11 (2011), 4063-4071.

P. Novo, F. Volpetti, V. Chu and J. P. Conde, "Control of Sequential Fluid Delivery in a Fully Autonomous Capillary Microfluidic Device", Lab Chip, 13 (2013), 641-645.

Search report dated Jul. 31, 2012 for Portuguese provisional patent application No. 106365, National Industrial Property Institute (INPI), Portugal; see in particular p. 3.

* cited by examiner

AUTONOMOUS AND PROGRAMMABLE SEQUENTIAL FLOW OF SOLUTIONS IN CAPILLARY MICROFLUIDICS

TECHNICAL FIELD

The present disclosure relates in general to microfluidic devices and more specifically to capillary microfluidic devices that do not require external pumping and valving systems to cause a liquid to flow.

BACKGROUND ART

In the scientific community, many developments in capillary microfluidics have the goal of producing point-of-care (PoC) devices for biomedical applications (e.g., detection of C-reactive protein based on a fluorescence immunoassay using a fluorescence microscope), food safety applications (e.g., detection of botulinum toxin based on an integrated capillary electrochemical sensor), or scientific research applications. These devices often employ biosensors that require the flow (and/or incubation) of different solutions (including the solution under test) in a sequential order at appropriate flow rates and/or periods of time.

As a specific example, a PoC device may utilize lateral flow strips. A common lateral flow strip is simple device that only requires the placement of a drop of a sample under test on an extremity of the strip. Consequently the fluid flows in the direction of the other extremity during which a cascade of events is responsible for the analysis of the sample analytes and signal production. Example applications of the lateral flow in biomedical diagnostics are for pregnancy tests and glycemia monitoring. Other applications include systems to monitor food and beverage safety, biological threat and environmental toxins.

DISCLOSURE OF INVENTION

According to aspects of the present disclosure, a system for the analysis of liquids comprises a microfluidic device having at least two inlets, an outlet and a microfluidic channel that connects the first inlet and the second inlet to the outlet. For instance, an exemplary implementation of the microfluidic device has at least a first inlet that is open and a second inlet that is open. The microfluidic channel has at least one microfabricated structure that confines liquids flowing through the microfluidic channel to the outlet. Moreover, the microfluidic device is configured such that the first inlet is positioned closer to the microfluidic channel than the second inlet. In operation, a specific volume of liquid placed in the respective first and second inlets flows autonomously such that the liquid in the first inlet flows into the microfluidic channel by capillary forces, and the liquid in the second inlet subsequently flows (i.e., flows sequentially) into the microfluidic channel behind the liquid from the first inlet.

The microfluidic device may have a region that connects the first inlet to the second inlet upstream of the microfluidic channel. In this exemplary implementation, entrapped air, i.e., an air bubble, may separate the liquid from the first inlet from the liquid from the second inlet. As the liquids flow to the outlet through the microfluidic channel, the liquid from the second inlet may remain separated from the liquid from the first inlet by the entrapped air. Alternatively, there may be no entrapped air present between the liquids present in the microfluidic channel.

MODES FOR CARRYING OF THE INVENTION

According to aspects of the present disclosure, a miniaturized capillary-based microfluidic device is provided, which integrates a dynamic strategy for the sequential delivery of controlled volumes of liquids with autonomous microfluidic operation. Autonomous microfluidic operation is implemented through capillarity by confining the flow of the sequentially delivered liquids through a microfluidic channel. Further aspects provide for the autonomous and sequential advancement of the liquids as samples that are kept separate or otherwise distinct from the other samples as the liquids pass through the microfluidic channel, e.g., to avoid the liquids from mixing.

For instance, in an illustrative implementation, the capillary microfluidic device requires only the placement of each sample of liquid at a corresponding inlet. In a particular example, the microfluidic device utilizes at least two inlets (e.g., a first inlet and a second inlet) each open to the air. The two inlets are sequentially connected to at least one sealed microfluidic channel having a microfabricated structure that is not open to the air. The positioning of the inlets relative to the microfluidic channel(s) provides for the programmed sequence of fluid flow by means of capillarity without the use of valves.

Referring now to the drawings and in particular to FIGS. 1A-1F generally, schematic top views are provided of a microfluidic device 100, which is presented according to aspects of the present disclosure.

Figure 1A:
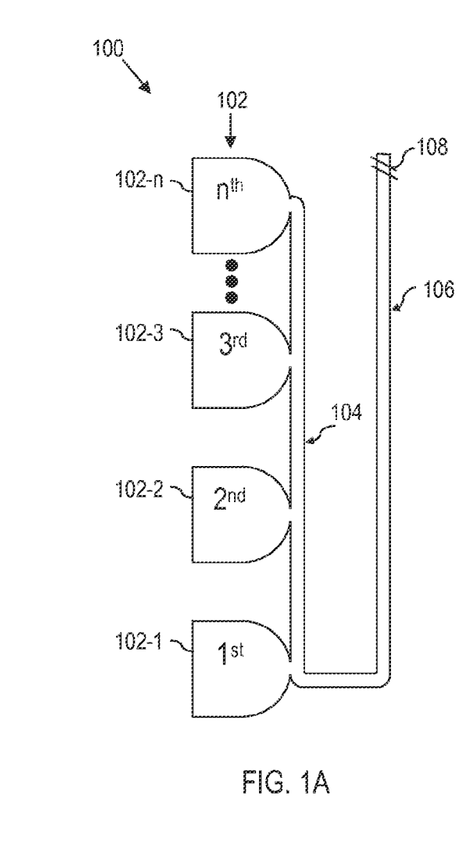
FIG. 1A is a microfluidic device according to aspects of the present disclosure.

With reference to FIG. 1A, a microfluidic device 100 includes a plurality of solution inlets 102 (e.g., implemented as insertion reservoirs). In an exemplary implementation, each inlet 102 is open to the air. In practice, each inlet 102 may be open (e.g., to the air) either directly or indirectly, such as through other channels, apertures, couplers, passageways or other suitable structures. As illustrated, there are n inlets 102 where n is any reasonable positive integer greater than one. Aspects of the present disclosure can be scaled up to any number of inlets 102 necessary for a particular application. For example of a microfluidic structure having four inlets 102 may be utilized for performing an enzyme-linked immunosorbent assay (ELISA).

As used herein, the inlets are referenced generally by the reference numeral 102. However, individual or specific inlets are further identified by a reference using a hyphen and a sequential integer. The sequential integer identifies the sequence or position of the particular inlet relative to other inlets 102. Thus, 102-1 is the first in-line inlet, 102-2 is the second in-line inlet, 102-3 is the third in-line inlet and 102-n is the nth inlet in the sequential line of inlets.

Each inlet 102 couples to at least one sealed microfluidic structure (i.e., not open to the air), which provides for the programmed sequence of fluid flow as will be described in greater detail herein. For instance, as illustrated, each inlet 102 couples in parallel to a liquid receiving region 104 that is closed to the air. The liquid receiving region 104 in turn, sequences the inlets 102 serially based upon the in-line position of each inlet 102, e.g., as illustrated, the inlets 102 are ordered in the sequence 102-1, 102-2, 102-3 . . . 102-n. In practice, each inlet 102 may couple to the liquid receiving region 104 via any suitable means, including direct coupling, or indirect coupling through any intervening passageways, devices, etc. For instance, as illustrated, each inlet 102 includes a port that allows liquid within the inlet to flow through its port to the liquid receiving region 104.

Additionally, in the illustrated implementation, the liquid receiving region 104 provides a single passageway to a common microfluidic channel (also referred to herein as the connecting channel) 106. As such, the liquid receiving region 104 may extend from the inlet 102 placed in the last in-line position (inlet 102-n as illustrated) passing through the remaining inlets 102 to the microfluidic channel 106. The microfluidic channel 106 couples to an outlet 108, which can be used to couple the microfluidic device 100 to other fluidic structures, as will be described in greater detail herein.

The microfluidic channel 106 has a constricted microchannel, e.g., a channel defined by at least one microfabricated structure that confines liquids flowing through the microfluidic channel. For instance, the microfabricated structure may include a channel or channel portion with reduced characteristic dimensions (e.g., on the order of 1-1,000 μm) in which capillary forces are especially strong, thus providing capillary flow and control or equivalent. The microfluidic channel 106 may also include other microstructures such that the microfluidic channel 106 further provides a controlled flow rate of liquids through the microfluidic channel 106. In this regard, the microfluidic channel 106 uses capillarity to control the flow of liquids from the inlets 102 to the liquid receiving region 104, through to the outlet 108 (which may be open to the air).

FIG. 1A illustrates the basic structure of the microfluidic device 100, where the inlets 102 are empty of liquids.

Figure 1B:
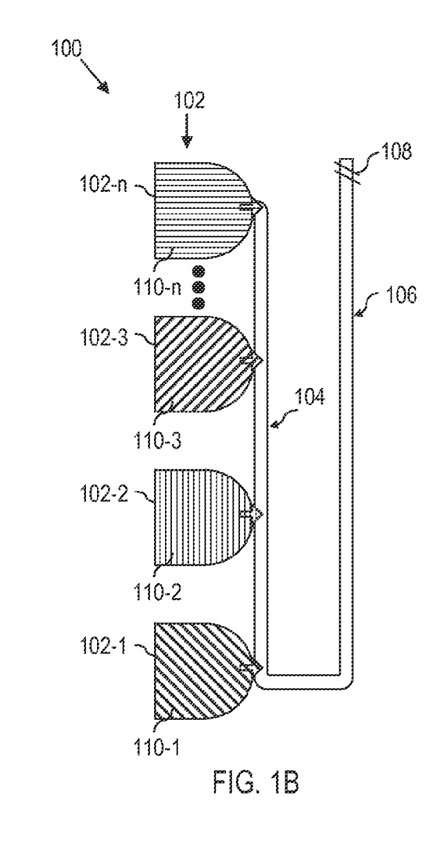
FIG. 1B is the microfluidic device of FIG. 1A, having liquids in each inlet, according to aspects of the present disclosure.

Referring to FIG. 1B, liquid is placed in each of the inlets 102. The liquid is referenced generally by the reference numeral 110. However, when referencing the liquid in a specific inlet 102, the liquid is further identified by a reference using a hyphen and a further integer matching that of the corresponding inlet 102. Thus, 110-1 is the liquid 110 in the first inlet 102-1, 110-2 is the liquid 110 in the second inlet 102-2, 110-3 is the liquid 110 in the third inlet 102-3 and 110-n is the liquid 110 in the nth inlet 102-n.

A user may insert the liquid(s) into the inlets manually. Alternatively, an automated process may be used to fill the inlets 102. For sake of discussion herein, each inlet 102 is filled with a different liquid, and is thus represented by different cross-hatching. In practice, each inlet 102 may be filled with the same or a different liquid as the remainder of the inlets 102. Moreover, each inlet 102 may be filled by the same general type of liquid, but from a different batch, sample, patient or other source. For instance, in an illustrative implementation, each solution required in an immunoassay is placed at the inlet corresponding to its immunoassay step number (e.g., the washing and blocking solution is placed at the first inlet 102-1, etc.) using micropipettes.

The liquid at the inlet 102 closest to the sealed microfluidic channel 106 will flow first while the remaining liquids are kept queued in sequence. When the previous liquid in the sequence is finished flowing out of its inlet, the liquid in the next position will flow.

Figure 1C:
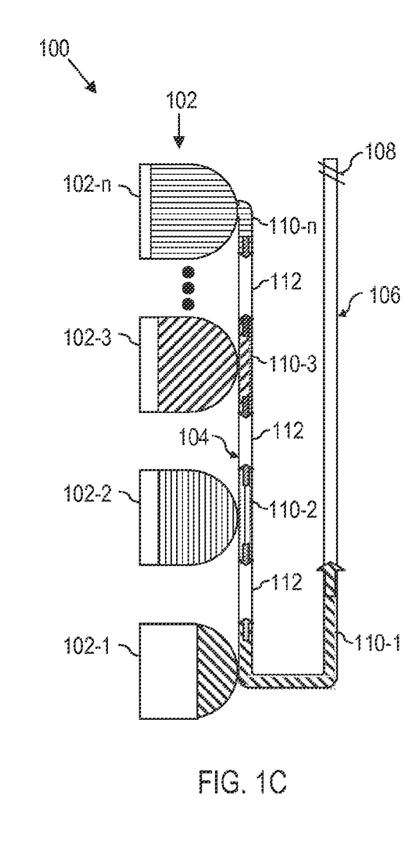
FIG. 1C is the microfluidic device of FIG. 1A, where the liquid from the first inlet flows by capillarity into a microfluidic channel, according to aspects of the present disclosure.

For instance, referring to FIG. 1C, the liquid 110 closest to the microfluidic channel 106, i.e., the liquid 110-1 in the inlet 102-1, (as identified with the left to right downward diagonal cross hatch) can flow continuously from the inlet 102-1 to the microfluidic channel 106, as schematically represented. In practice, the liquid 110-1 from the inlet 102-1 may flow until the inlet 102-1 is emptied of the liquid 110-1. Moreover, while the liquid 110-1 flows from the inlet 102-1 through the microfluidic channel 106 by capillarity, the liquid from other inlets 102-2 through 102-n is temporarily stopped within the region 104 so as to form a queue/line such that each liquid 110-2 through 110-n is separated within the region 104, i.e., does not mix.

In the illustrative implementation, pockets of entrapped gas are used to maintain separation of the liquids while queued for movement to the microfluidic channel 106. For instance, in the illustrative implementation, the inlets 102 are open to the air. Thus, air bubbles 112 may be allowed to form, which separate the liquid 110 from each inlet 102 that flows into the region 104. As used herein, the term "air bubble" is used generally for descriptive purposes to refer to entrapped gas. However, the gas is not limited to air per se.

When the liquids 110 flow through the microfluidic channel 106, each air bubble 112 may persist through the microfluidic channel 106 and other downstream processes. Alternatively, the microfluidic device 100 may incorporate an air evacuation mechanism that evacuates any entrapped air that separates the liquid of adjacent inlets 102. Thus, the air bubbles 112 may evacuate from the device such that no air bubbles are present through the microfluidic channel 106, outlet 108 or other downstream processes. As a few illustrative examples, an air evacuation mechanism may be implemented by the inlets themselves. In this regard, the air bubbles 112 may escape as the liquid passes a previously emptied inlet 102. For instance, when liquid 110-1 is finished at its corresponding inlet 102-1 the bubble 112 separating liquid 110-1 and 110-2 may evacuate through inlet 102-1. At that moment liquids 110-1 and 110-2 will touch and flow in the microfluidic channel 106. Alternatively, an air evacuation mechanism may be implemented by structures built into or otherwise coupled to the liquid receiving region 104, e.g., that may diffuse or otherwise evacuate the entrapped air bubbles 112 from the microfluidic device 100. Still further, an air evacuation mechanism may be implemented by any other suitable evacuation strategy.

Notably, in the illustrated exemplary implementation, to a limited degree, each inlet 102 begins to empty into the region 104. However, the amount of liquid allowed to exit the associated inlet 102 and flow into the region 104 is limited based upon the dimensions of the region 104. That is, region 104 provides enough space to allow liquid 110 and corresponding separating air bubbles 112 to "queue up" waiting for the preceding inlet 102 to empty into the microfluidic channel 106.

Figure 1D:
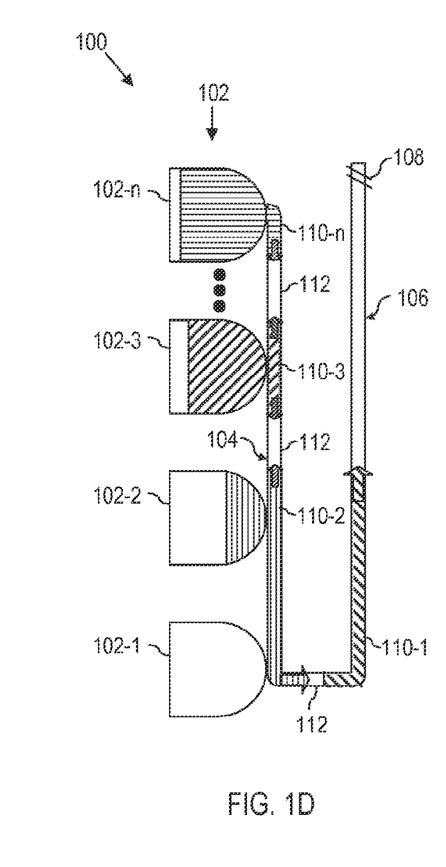
FIG. 1D is the microfluidic device of FIG. 1A, where the liquid from the first and second inlets flow by capillarity into the microfluidic channel, according to aspects of the present disclosure.

Referring to FIG. 1D, when the liquid of the first inlet 102-1 is finished emptying into the microfluidic channel 106 via capillarity, the next liquid in line (liquid 110-2 in the second inlet 102-2 as represented by the vertical cross-hatch) can flow by capillarity from the second inlet 102-2, through the region 104 and into the microfluidic channel 106. Thus, the liquid 110-2 from the second inlet 102-2 sequentially follows the liquid 110-1 from the first inlet 102-1.

For purposes of clarity of discussion herein, the liquid 110-2 is separated from the liquid 110-1 by a corresponding air bubble 112 in region 106. However, in practical applications, there is no requirement that an air bubble 112 persist into region 106.

Figure 1E:
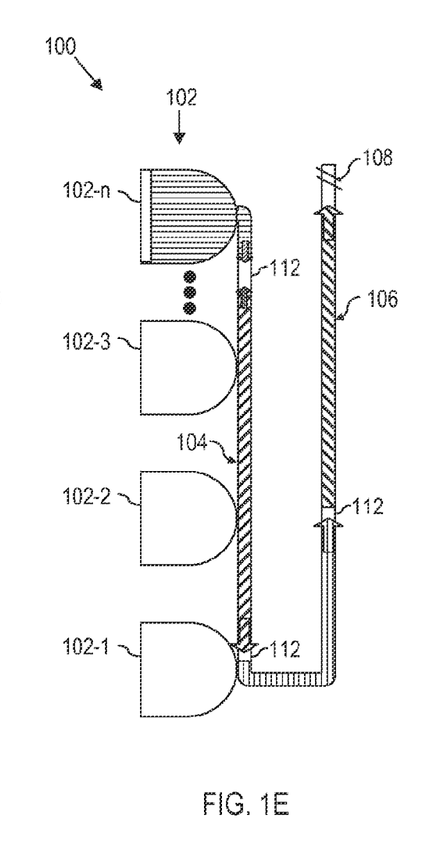
FIG. 1E is the microfluidic device of FIG. 1A, where the liquid from the first, second and third inlets flow by capillarity into the microfluidic channel, according to aspects of the present disclosure.

Referring to FIG. 1E, when the liquid of the second inlet 102-2 is finished emptying into the microfluidic channel 106, the next liquid in line (liquid 110-3 in the third inlet 102-3 as represented by the left to right upward diagonal cross-hatch) can flow from the third inlet 102-3, through the region 104 and into the microfluidic channel 106 by capillarity. Thus, the liquid 110-3 from the third inlet 102-3 sequentially follows the liquid 110-2 from the second inlet 102-2, optionally separated therefrom in the microfluidic channel 106 by an air bubble 112.

Figure 1F:
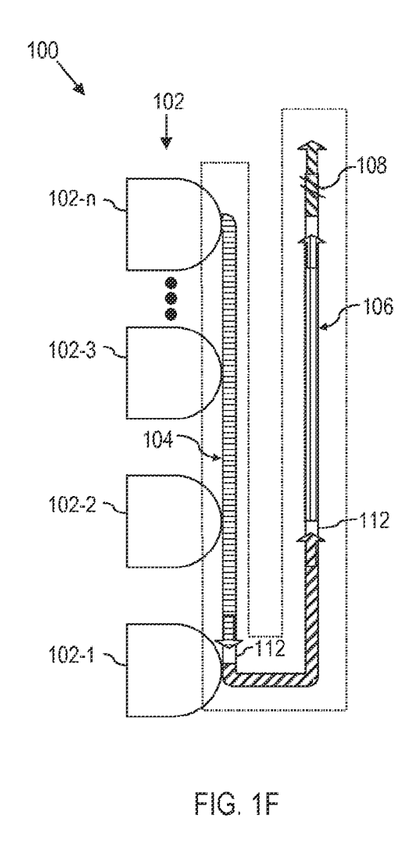
FIG. 1F is the microfluidic device of FIG. 1A, where the liquid from each inlet flows by capillarity into the microfluidic channel, according to aspects of the present disclosure.

Referring to FIG. 1F, when the liquid from all but the last in-line inlet 102 (102-$n$ in this illustrative example) is finished emptying into the microfluidic channel 106, the last liquid in line (liquid 110-$n$ in the nth inlet 102-$n$ as represented by the horizontal cross-hatch) can flow from the nth inlet 102-$n$, through the region 104 and into the microfluidic channel 106 by capillarity. Thus, the liquid 110-$n$ from the nth inlet 102-$n$ sequentially follows the preceding liquid 110, optionally separated therefrom in the microfluidic channel 106 by an air bubble 112.

In general, in certain conventional systems, air bubbles are problematic, resulting in failure of the microfluidics proper functioning (as an example, conventional processes typically impose a necessity to remove air bubbles from sealed channels of a test system). However, aspects of the present disclosure utilize inherent inter-inlet entrapped air to physically separate fluids (at least in region 104) thus preventing fluid mixing. The solution volume at the respective inlets 102 flows autonomously and sequentially into the capillary microfluidic device by capillary forces. Thus, eventually, all of the inlets 102 will sequentially empty into the region 104 and corresponding microfluidic channel 106. Thus, the sequence of liquid flow is programmed by its inlet position relative to the microfluidic channel 106.

Aspects of the present disclosure provide a high level of fluid control due to the confinement of fluids in microfabricated structures. Therefore, aspects of the present disclosure can be designed for generalized implementation or selectively optimized for specific applications of very precise liquid input/output specifications.

Figure 2:
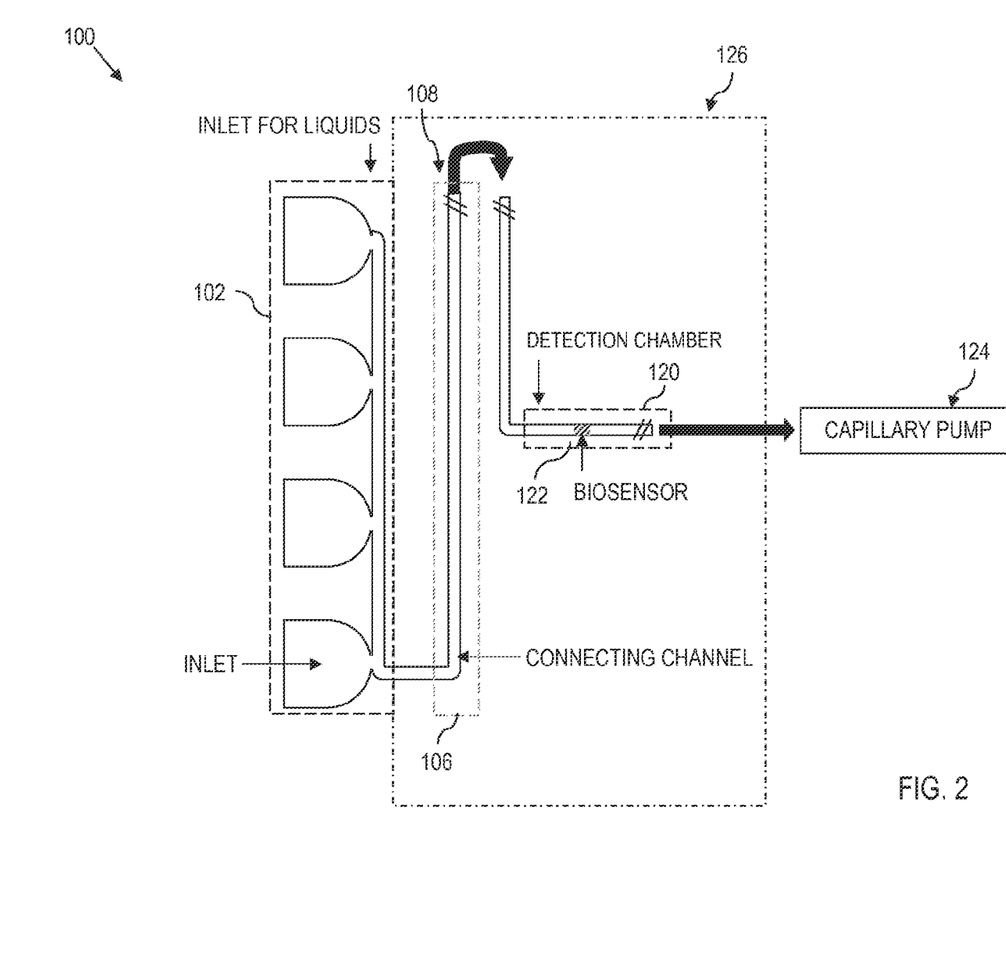
FIG. 2 an exemplary system where the microfluidic device of FIG. 1A is integrated with another fluidic structure, according to aspects of the present disclosure.

Referring to FIG. 2, the microfluidic device 100 may be integrated with other fluidic structures. For instance, as noted in greater detail herein, aspects of the present disclosure can be monolithically integrated or fabricated as an external module and integrated with other fluidic structures through connection to the outlet 108. In the illustrative example, a fluidic structure has at least one detection (i.e., reaction) chamber 120 where at least one biosensor location 122 provides a biosensor that is responsible for the detection of analytes of interest. Detection and quantification of the biosensor resulting signals is performed by integrating signal transducers.

As schematically represented, continuous fluid flow is provided by at least one capillary pump 124. For instance, continuous flow can be provided by the capillary pump 124 (or pumps) operating at a constant flow rate, e.g., 0.30+/− 0.04 $\mu L\ min^{-1}$ in an illustrative implementation. When the liquid 110-1 (which flows to the fluidic structure via capillarity) has been exhausted, the solution front is already at the capillary pump 124, which provides continuous flow of the remaining liquids 110-2 through 110-$n$.

Although illustrated as a separate device for clarity of disclosure, the capillary pump 124 may in practice, be implemented by a microfluidic channel in a manner analogous to the microfluidic channel 106. Moreover, the capillary pump 124 may in practice, be implemented as a single microfluidic channel or a combination of one or more microfluidic channels, which may be positioned upstream, downstream or both, relative to the detection chamber 120. The capillary pump 124 may alternatively be a separate device, or the capillary pump 124 may be implemented by other structures or features. In this regard, the capillary pump 124 may be utilized to keep the flow present so that the solutions do not stop when they reach the biosensor area 122.

As an example, the capillary pump 124 may consist of a microstructure that includes posts of rounded and interlocked hexagons to obtain approximately constant flow rates. In porous materials or capillaries of reduced characteristic dimensions, fluids can flow by a combination of surface liquid adhesion and liquid-liquid cohesive forces. Adhesion forces are responsible for pulling the fluid front, while the cohesive forces are responsible for the propagation of the capillary pressure to the bulk liquid. In an exemplary implementation, a capillary liquid flow rate of 0.30+/−0.04 $\mu L$ $min^{-1}$ was realized.

According to further aspects of the present disclosure, the inlets 102 are connected in a configuration that places each successive inlet 102 further away from the detection chamber 120. Correspondingly, solution flow is programmed sequentially in order as a function of corresponding inlet position (relative to the microfluidic channel 106) towards the detection. chamber 120. Moreover, programming of the liquid flow time is tuned by adjusting the volume of liquid 110 at the inlets 102 and the (upstream) liquid flow rate set by the capillary pump 124. In practical applications, the microfluidic device 100 may also optionally consider the volume of liquid 110 which evaporates prior to the start of its flow (this parameter can be adjusted by local control of the humidity and temperature parameters and also by the device design).

With reference to FIGS. 1-2 generally, a complete fluidic system is provided, comprising the microfluidic device 100 and at least one other fluidic structure, which can be used to carry out biosensing experiments, such as immunoassays for the detection of analytes of clinical, environmental, and food safety importance, among others. As further examples, fluidic structures can be used to implement biosensor strategies that employ for instance, nucleic acid, antibody, enzyme, cell, polymer, or other sensing principle strategies. In this regard, the detection of biosensing resulting signals is performed by integrating the signals read out from microfabricated sensors.

An optional polydimethylsiloxane (PDMS) sheet 126 may be utilized to cover the region 104, the microfluidic channel 106, the outlet 108, the reaction chamber 120 or combinations thereof. The PDMS sheet seals the corresponding microfluidic structures that it covers. In another exemplary implementation, the capillary microfluidic device 100 may be microfabricated in PDMS, e.g., using soft lithography.

Referring to FIG. 3A-3D generally, a schematic diagram illustrates an example implementation of an immunoassay biosensor for analyte detection and quantification.

Figure 3A:
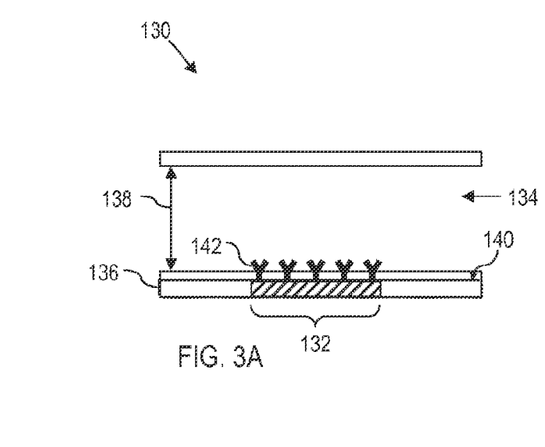
FIG. 3A is a schematic diagram illustrating the preparation of a microfluidic biosensor in an exemplary implementation of an immunoassay biosensor for analyte detection and quantification, according to aspects of the present disclosure.

Referring specifically to FIG. 3A, a schematic diagram 130 illustrates the preparation of a microfluidic biosensor. As illustrated, a biosensor is positioned at a biosensor location 132 along a microchannel 134. The biosensor location 132 may correspond, for instance, to the patterned area, corresponding to biosensor location 122, of FIG. 2.

More particularly, the microchannel 134 has a microchannel surface 136 and a microchannel height 138. A (non-specific) adsorption prevention coating 140 lines the inner wall of the microchannel surface 136, at least in the area over the biosensor location 132. For instance, an adsorption prevention coating may include a suitable agent, such as bovine serum albumin, polyethylene glycol, etc. In the illustrative implementation, the biosensor provides for the immobilization of probe antibodies 142.

Figure 3B:
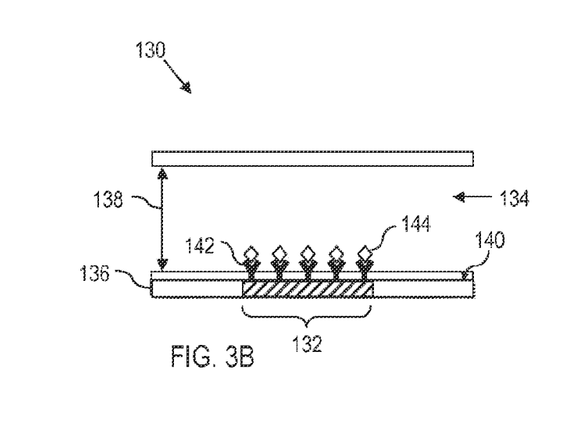
FIG. 3B is a schematic diagram illustrating the flow of a sample under analysis in the biosensor of FIG. 3A, according to aspects of the present disclosure.

Referring to FIG. 3B, a schematic diagram illustrates the flow of a sample under analysis in the biosensor of FIG. 3A, according to aspects of the present disclosure herein. As illustrated, the probe antibodies have captured analytes 144 (represented by the diamond shapes).

Figure 3C:
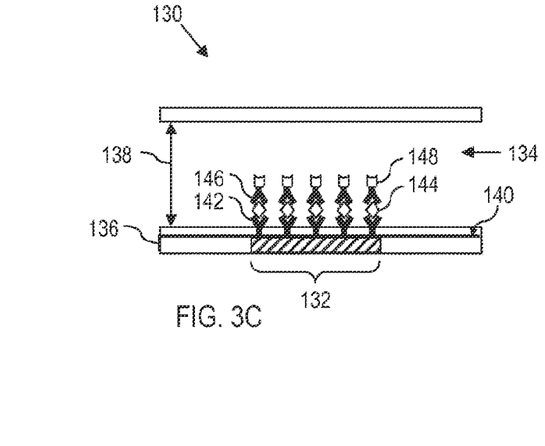
FIG. 3C is a schematic diagram illustrating the transduction of the analyte amount into a detectable optical signal in the biosensor of FIG. 3A, according to aspects of the present disclosure.

Referring to FIG. 3C, a schematic diagram illustrates the transduction of the analyte amount into a detectable optical signal in the biosensor of FIG. 3A, according to aspects of the present disclosure herein. As illustrated, the analytes 144 captured by the probe antibodies each attract a secondary antibody 146 (represented by the caret symbol), which is bound to a label 148 (e.g., fluorophore, enzyme).

Figure 3D:
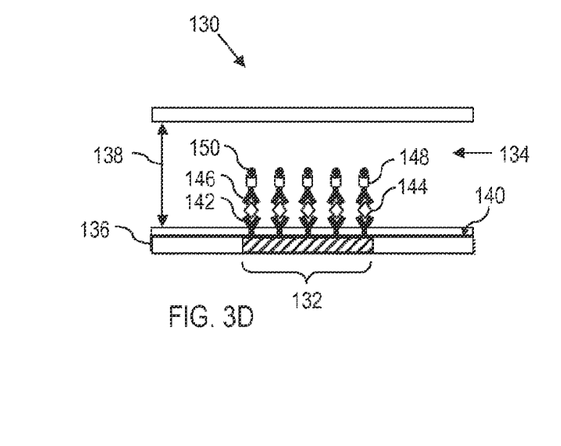
FIG. 3D is a schematic diagram illustrating the addition of enzyme substrates in case of using enzyme labels in the biosensor of FIG. 3A, according to aspects of the present disclosure.

Referring to FIG. 3D, a schematic diagram illustrates the addition of enzyme substrates 150 in case of using enzyme labels in the biosensor of FIG. 3C, according to aspects of the present disclosure herein. For instance, in an exemplary yet illustrative implementation, colorimetrics is utilized to determine the concentration of a substance that is in a liquid, e.g., one of the liquids 110-1 through 110-n. For instance, the addition of an enzyme substrate, colorimetry (e.g., 3,3',5,5'-Tetramethylbenzidine or TMB) or chemiluminescence e.g., Luminol) are examples of optical detection of light absorption or generation, respectively.

Figure 4A:
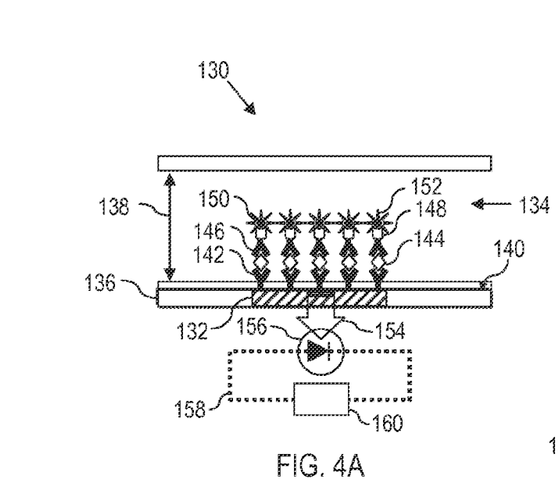
FIG. 4A is a schematic representation of an exemplary implementation for the transduction of an immunoassay biosensor analyte concentration into optical signals using chemiluminescence, according to aspects of the present disclosure.
Figure 4B:
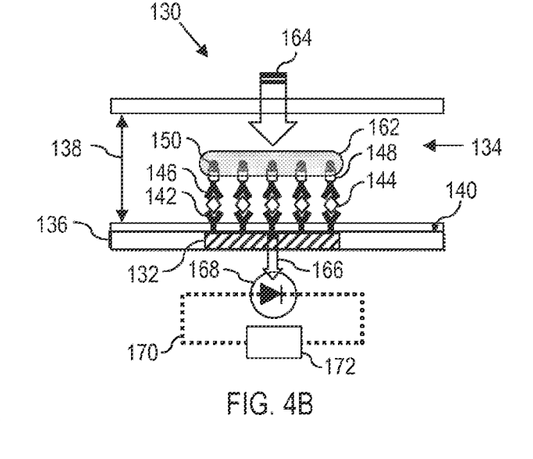
FIG. 4B is a schematic representation of an exemplary implementation for the transduction of an immunoassay biosensor analyte concentration into optical signals using colorimetry, according to aspects of the present disclosure.
Figure 4C:
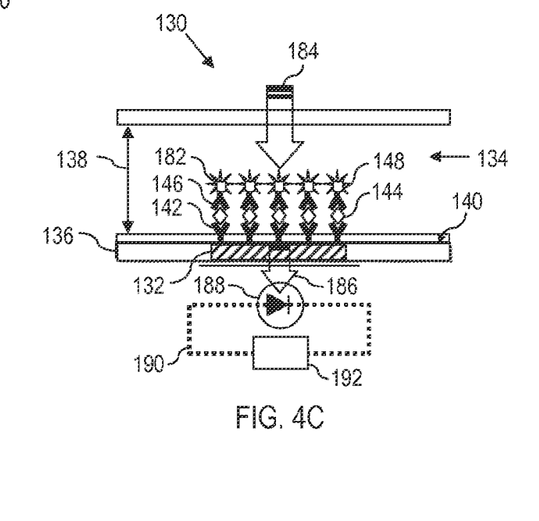
FIG. 4C is a schematic representation of an exemplary implementation for the transduction of an immunoassay biosensor analyte concentration into optical signals using fluorescence, according to aspects of the present disclosure.

Referring generally to FIGS. 4A-4C, examples of implementations of the transduction of an immunoassay biosensor analyte concentration into optical signals is provided. The schematic representations of FIGS. 4A-4C can correspond with the immunoassay biosensor of FIGS. 3A-3D, and correspondingly, with the biosensor 122 of FIG. 2.

Referring to FIG. 4A, an example implementation of the transduction of an immunoassay biosensor analyte concentration into optical signals is provided, using chemiluminescence. More particularly, FIG. 4A illustrates catalysis 152 of a chemiluminescent substrate 150 by the label 148 (e.g., a suitable enzyme). Moreover, as illustrated, the chemiluminescence signal is illustrated at 154 reaching a photosensor 156. An electrical connection 158 carries the output of the photosensor 156 to a device 160 for photosensor monitoring and signal measurement. In this regard, the device 160 is configured for chemiluminescent analysis.

Referring to FIG. 4B, an example implementation of the transduction of an immunoassay biosensor analyte concentration into optical signals is provided, using colorimetry. FIG. 4B illustrates catalysis 162 of a colorimetric substrate 150 by the label 148, e.g., a suitable enzyme. Excitation light 164 from a suitable source (not shown) is transmitted through the microchannel and exits through the biosensor location 132 and through the microchannel surface 136 as light 166. In an analogous manner to that of FIG. 4A, the example implementation of FIG. 4B includes a photosensor 168, and an electrical connection 170 that carries the output of the photosensor 168 to a device 172 for photosensor monitoring and signal measurement. In this regard, the device 172 is configured for colorimetric analysis.

Referring to FIG. 4C, an example implementation of the transduction of an immunoassay biosensor analyte concentration into optical signals is provided, using fluorescence. FIG. 4C illustrates fluorescence label 182 (e.g., fluorophore) attached to each secondary antibody 146. The example implementation includes an excitation light 184 from a suitable excitation source (not shown). The excitation light 184 is transmitted through the microchannel and exits through the biosensor location 132 and through the microchannel surface 136 as fluorescence light 186. In an analogous manner to that of FIG. 4A, the example implementation of FIG. 4C includes a photosensor 188 and an electrical connection 190 that carries the output of the photosensor 188 to a device 192 for photosensor monitoring and signal measurement. In this regard, the device 192 is configured for fluorescence analysis.

Example Implementation:

In an illustrative exemplary implementation, liquid inlets 102, a liquid receiving region 104, a microfluidic channel 106, a detection chamber 120 and capillary pumps 124 were microfabricated by soft lithography using SU-8 molds. Probe IgG antibodies were spotted onto the open detection chamber. The microfabricated network was then sealed to a thin flat PDMS sheet, leaving open an access for the inlets and an opening at the exit of the capillary pumps to allow liquid flow and evaporation. Confirmation and calibration of the assay was made with fluorescence microscopy.

More particularly, the process included the fabrication of a 20 μm thick SU-8 photoresist mold on top of a silicon substrate. The SU-8 photoresist was selectively exposed to UV light through an aluminum mask on quartz and was subsequently developed. The SU-8 mold was then aligned with a set of micromachined PMMA plates that define the overall shape of the PDMS chip (w=2.5 cm; h=2 mm; l=4 cm). A 1:10 (w/w) mixture of curing agent and base PDMS was poured in the molds and allowed to cure for 2 hours at 60 degrees Celsius. Both PDMS capillary microfluidic chips and flat 200 μm thick PDMS sheets (used for sealing of the microstructures) were submitted to 60 minutes of UV-ozone treatment to oxidize the PDMS surface and control its hydrophilic characteristics. After oxidation, the average measured contact angle on a flat surface was 40 degrees plus or minus 5 degrees.

The antibody solutions were spotted onto the open detection chamber 120 using a non-contact spotter. Antibody solutions were spotted using a piezoelectric pipette, which is mounted on a computer-controlled stage, allowing the alignment of the spots with the substrate features with precision and accuracy of approximately 7 and approximately 8 μm respectively. Individual spots of 4.5 nL of antibody solution, with an average diameter of 300 μm, were spotted along the detection chamber 120. The use of integrated alignment marks allowed for alignment of the microspots in the detection chamber.

During the spotting of antibody solutions, the temperature was fixed at 16 degrees Celsius and the humidity was adjusted to near the dew point to decrease the evaporation rate of the droplets. The solution droplets were spotted off-center, leaving a section of the microfluidic channel cross section open. This is fundamental in non-dry spot situations since a fully wetted microfluidic channel cross-section could prevent the initial flow of the inlet solutions. After the liquids have reached the capillary pump this is no longer a problem. The micro-spotted droplets were allowed to incubate for 30 minutes prior to sealing. The microfluidic channels were then sealed with the flat PDMS sheet.

Figure 5A:
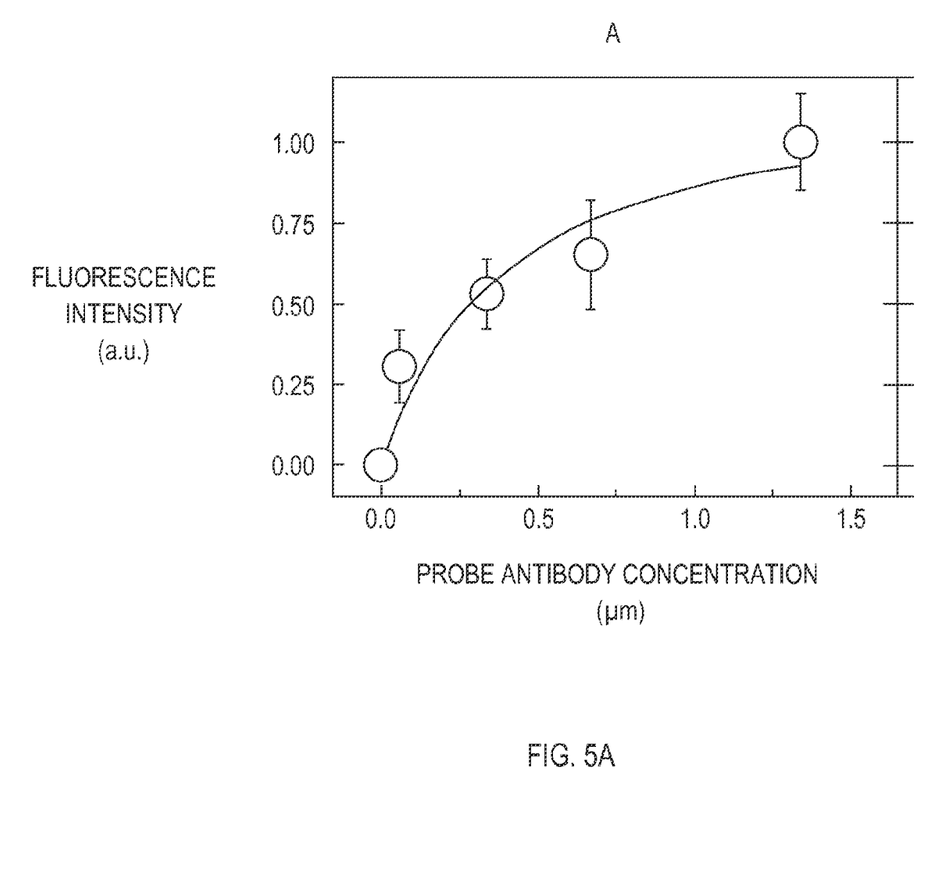
FIG. 5A is a chart illustrating a resulting fluorescence intensity acquired by the biosensor after completion of an exemplary autonomous capillary immunoassay.

Referring to FIG. 5A, a chart shows an antibody adsorption profile of exemplary spotted antibody solutions. The chart illustrates fluorescence intensity as a function of the concentration of the probe antibody solution (keeping constant concentration of the target antibody solution 1.3 μM). A fit to the results was made using the Langmuir model of adsorption.

$$F = K\theta_{max}C/(KC+1) \quad \text{(Equation 1)}$$

Where F is the fluorescence intensity, $\theta_{max}$ is the maximum fluorescence value, K is a constant, and C is the antibody solution concentration. The fluorescence signal saturated for probe antibody solution concentrations of approximately 1.33 μM.

Figure 5B:
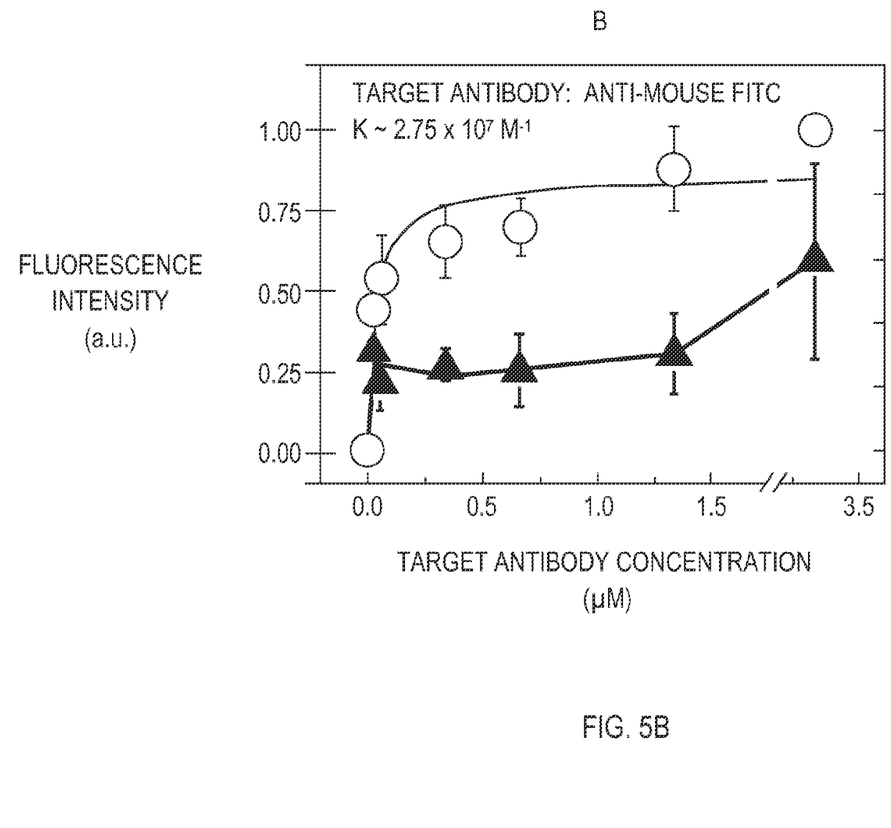
FIG. 5B is a chart illustrating a resulting fluorescence intensity profile as a function of an exemplary target antibody concentration, according to an exemplary aspect of the present disclosure.

Referring to FIG. 5B, a chart shows the fluorescence intensity at spots of adsorbed mouse and bovine IgG probe antibodies as a function of the concentration of the anti-mouse IgG-FITC target antibody solution in an exemplary test. Results of the specific detection of the mouse IgG were fit to equation 1 (above) and are shown. The line connecting the results of the non-specific detection of bovine IgG is a guide. Specific detection of the mouse IgG probe antibodies is clearly above the signal obtained tier the non-specific detection of the bovine IgG probe antibodies. The antibody affinity constant was obtained by fitting equation 1 to the specific detection results. The resulting affinity constant in an exemplary test was of $2.75 \times 10^7$ $M^{-1}$. At the highest concentrations of target antibody (3.33 μM) an increase in non-specific signals is observed, probably due to multilayer formation.

Miscellaneous:

Aspects of the present disclosure can be utilized with microfluidic structures for point of care (PoC) devices. For instance, the biosensor area (area 122 of FIG. 2 and area 132 of FIGS. 3A-3D) may be created by immobilization of probe antibodies. In this example, the channel walls are coated with a non-specific adsorption prevention agent (e.g., bovine serum albumin, polyethylene glycol). The analyte in the sample under analysis is captured by the antibody probes. An example of the transduction of the antigen amount detected and captured is the use of secondary antibodies containing labels. Examples of a label used in optical detection are fluorescence (e.g., FITC) or enzyme (e.g., horseradish peroxidase, alkaline phosphatase) labels. In the particular case of using enzyme labels the use of appropriate substrate solutions is required. Additionally, an example of the integrated optical detection and quantification of the optical signals is demonstrated in FIG. 4A, FIG. 4B and FIG. 4C. The fluidic device comprising aspects of the present disclosure and at least one reaction chamber with at least a biosensor location is integrated with at least one transducer for signal detection and quantification.

According to aspects of the present disclosure, capillary microfluidics systems are provided, which reduce the need for external pumping and valving systems as compared to other, conventional microfluidic strategies. As such, the capillary microfluidics systems herein reduce the complexity of integrated fluidic devices while increasing their portability. For instance, as described in greater detail herein, in illustrative implementations, the control of fluid flow is performed by a rational design of device channels and other fluidic structures together with the control of the wettability of the surface. Miniaturization has the potential advantages of portability, multiplexing, reduced sample and reactant volumes, speed, sensitivity, and cost.

What is claimed is:
1. A system for the analysis of liquids, the system comprising:
a microfluidic device having:
a first inlet that is open to air via a passageway and is implemented as a first insertion reservoir;
a second inlet that is open and is implemented as a second insertion reservoir;
an outlet;
a microfluidic channel that couples the first inlet and the second inlet to the outlet such that the first inlet is positioned closer to the microfluidic channel than the second inlet, where the microfluidic channel has at least one microfabricated structure that confines fluids flowing to the outlet; and
a liquid receiving region that connects the first inlet to the second inlet in parallel, where the liquid receiving region further couples each of the first and second inlets to the microfluidic channel serially based upon an in-line position of each of the first and second inlets relative to the microfluidic channel, so as to provide for a serial fluid flow in a programmed sequence through the microfluidic channel to the outlet;
wherein:

a structure of the first inlet, including the passageway of the first inlet, is sufficiently open to air so as to enable inter-inlet entrapped air to physically separate fluids in the liquid receiving region so as to prevent fluid mixing; and autonomous microfluidic operation is implemented by a confined flow of a specific volume liquid placed in the respective first and second inlets that is sequentially delivered by the liquid receiving region to the microfluidic channel by capillarity without requiring the use of a valve.

2. The system according to claim 1, wherein the microfluidic channel is sealed.

3. The system according to claim 1 wherein the microfluidic device further comprises:
a channel portion with reduced characteristic dimensions for providing capillary flow and control or equivalent; and
an air evacuation mechanism that evacuates any entrapped air that separates the liquid of the first and second inlets.

4. The system according to claim 1, wherein the outlet is sequentially connected to a sealed microfluidic structure comprising:
a reaction chamber having at least one biosensor.

5. The system according to claim 4, wherein the biosensor comprises:
a microchannel surface; and
an adsorption prevention coating that lines the inner wall of the microchannel surface.

6. The system according to claim 4, wherein the biosensor comprises:
a device transduction of an immunoassay biosensor analyte concentration into optical signals.

7. The system according to claim 6 further comprising:
a photosensor; and
an electrical connection that carries an output of the photosensor to a photosensor monitoring and signal measurement device.

8. The system according to claim 7, wherein:
the photosensor monitoring and signal measurement device is configured for chemiluminescent analysis.

9. The system according to claim 7, wherein:
the photosensor monitoring and signal measurement device is configured for colorimetry.

10. The system according to claim 7, wherein:
the photosensor monitoring and signal measurement device is configured for fluorescence.

11. The system according to claim 1, wherein the microfluidic device is monolithically integrated with at least one other fluidic structure through the microfluidic channel.

12. The system according to claim 1, wherein the microfluidic device is an external module that interfaces with at least one other fluidic device through the microfluidic channel.

13. The system according to claim 1, wherein:
the microfluidic device further includes a third inlet that is open and is implemented as a third insertion reservoir coupled to the liquid receiving region;
wherein:
the liquid receiving region connects the third inlet to the microfluidic channel serially based upon an in-line position the third inlet behind the second inlet relative to the microfluidic channel; and
a specific volume liquid placed in the third inlet flows autonomously such that the liquid in the third inlet automatically flows sequentially into the microfluidic channel after the liquid from the second inlet flows into the microfluidic channel.

14. The system according to claim 13, wherein:
the liquid receiving region connects the third inlet in parallel with the first inlet and the second inlet,
the liquid receiving region further couples each of the third inlet in-line with the first inlet and the second inlet relative to the microfluidic channel;
the first inlet is coupled to the receiving region closer to the microfluidic channel than the second inlet and the third inlet; and
the second inlet is coupled to the receiving region between the first inlet and the third inlet.

15. A method for analysis of liquids, the method comprising:
providing a microfluidic device having:
a first inlet that is open to air via a passageway and is implemented as a first insertion reservoir;
a second inlet that is open and is implemented as a second insertion reservoir;
an outlet;
a microfluidic channel that couples the first inlet and the second inlet to the outlet such that the first inlet is positioned closer to the microfluidic channel than the second inlet, where the microfluidic channel has at least one microfabricated structure that confines fluids flowing to the outlet; and
a liquid receiving region that connects the first inlet to the second inlet in parallel, where the liquid receiving region further couples each of the first and second inlets to the microfluidic channel serially based upon an in-line position of each of the first and second inlets relative to the microfluidic channel, so as to provide for a serial fluid flow in a programmed sequence through the microfluidic channel to the outlet;
providing a structure of the first inlet, including the passageway of the first inlet, that is sufficiently open to air so as to enable inter-inlet entrapped air to physically separate fluids in the liquid receiving region so as to prevent fluid mixing; and
placing liquid in the respective first and second inlets such that a specific volume of liquid placed in the respective first and second inlets flows via autonomous microfluidic operation by a confined flow that is sequentially delivered by the liquid receiving region to the microfluidic channel by capillarity without requiring the use of a valve.

16. The method according to claim 15, further comprising ensuring that the first reservoir is generally empty before allowing fluid from the second reservoir to enter the microfluidic channel by allowing an air bubble to form between the liquid from the first reservoir and the liquid from the second reservoir, wherein the air bubble prevents the liquid from the second reservoir from reaching the microfluidic channel before the first reservoir is generally empty.

17. The method according to claim 16 further comprising:
evacuating the air bubble through the first reservoir before the liquid from the second reservoir enters the microfluidic channel.

18. The method according to claim 15 further comprising:
allowing the air bubble to persist through to the microfluidic channel.

19. The method according to claim 15, wherein:
placing liquid in the respective first and second inlets comprises:

determining a sequential order for a first liquid, and a second liquid to be introduced to the microfluidic channel; and adding the first fluid to the first insertion reservoir, and the second fluid to the second insertion reservoir, wherein a determination of which fluid is added to which reservoir is based on the determined sequential order; and a specific volume of liquid placed in the respective first and second inlets flows autonomously, comprises:

using capillary action to initiate flow of the first liquid and the second liquid from their respective reservoirs to a receiving region of the microfluidic device at the same time;

using capillary action to allow flow from the receiving region to the microfluidic channel; and ensuring that the first reservoir is generally empty before allowing fluid from the second reservoir to enter the microfluidic channel from the receiving region.

* * * * *

UNITED STATES PATENT AND TRADEMARK OFFICE
CERTIFICATE OF CORRECTION

PATENT NO. : 9,931,630 B2
APPLICATION NO. : 14/405659
DATED : April 3, 2018
INVENTOR(S) : Virginia Chu et al.

It is certified that error appears in the above-identified patent and that said Letters Patent is hereby corrected as shown below:

On the Title Page

1 – Item (71) Applicants: delete the Applicants listed and replace with:
--Applicant: INSTITUTO DE ENGENHARIA DE SISTEMAS E COMPUTADORES PARA OS MICROSISTEMAS E AS NANOTECNOLOGIAS (INESC), Lisboa, PORTUGAL--;

2 – Item (72), Inventors should read:
--Virginia Chu, Lisboa (PT);
Pedro José De Oliva Novo, Romãs (PT);
João Pedro Estrela Rodriques Conde, Lisboa (PT);
Francesca Volpetti, Roma (IT)--;

In the Specification

3 – Column 6, Line 65, "surface liquid" should read --surface-liquid--; and

4 – Column 9, Line 66, "signal obtained tier the" should read --signal obtained for the--.

Signed and Sealed this
Third Day of July, 2018

Andrei Iancu
*Director of the United States Patent and Trademark Office*